United States Patent
Jeong et al.

(10) Patent No.: US 10,166,075 B2
(45) Date of Patent: Jan. 1, 2019

(54) MINIMALLY INVASIVE SURGICAL INSTRUMENT IMPLEMENTING A MOTOR

(75) Inventors: Chang Wook Jeong, Seoul (KR); Chun Chol Sin, Seoul (KR); Sung Ryul Kim, Seoul (KR); Hyung Tae Kim, Seoul (KR)

(73) Assignee: MOVASU, INC., Seoul (KR)

( * ) Notice: Subject to any disclaimer, the term of this patent is extended or adjusted under 35 U.S.C. 154(b) by 1358 days.

(21) Appl. No.: 14/113,212

(22) PCT Filed: Apr. 23, 2012

(86) PCT No.: PCT/KR2012/003124
§ 371 (c)(1),
(2), (4) Date: Jan. 6, 2014

(87) PCT Pub. No.: WO2012/144875
PCT Pub. Date: Oct. 26, 2012

(65) Prior Publication Data
US 2014/0350569 A1  Nov. 27, 2014

(30) Foreign Application Priority Data

Apr. 21, 2011  (KR) .................. 10-2011-0037442
Aug. 2, 2011  (KR) .................. 10-2011-0077110

(51) Int. Cl.
*A61B 34/00*  (2016.01)
*A61B 19/00*  (2006.01)
(Continued)

(52) U.S. Cl.
CPC .............. *A61B 19/22* (2013.01); *A61B 17/29* (2013.01); *A61B 34/71* (2016.02);
(Continued)

(58) Field of Classification Search
CPC .......... A61B 17/2909; A61B 17/00234; A61B 34/71; A61B 34/30; A61B 34/20;
(Continued)

(56) References Cited

U.S. PATENT DOCUMENTS 4,402,234 A * 9/1983 Malarz ................ B25J 19/0029
269/61
8,968,312 B2 * 3/2015 Marczyk ................ A61B 17/29
606/51
(Continued)

FOREIGN PATENT DOCUMENTS

KR  10-2007-0079052 A  8/2007
KR  10-2008-0021598 A  3/2008
KR  10-2010-0020373 A  2/2010

OTHER PUBLICATIONS

Korean Intellectual Property Office, International search report for International Application No. PCT/KR2012/003124, dated Nov. 28, 2012.

*Primary Examiner* — Diane Yabut
*Assistant Examiner* — Erich Herbermann
(74) *Attorney, Agent, or Firm* — Dinsmore & Shohl LLP; Yongsok Choi

(57) ABSTRACT

The present invention relates to a minimally invasive surgical instrument implementing a motor. According to one embodiment of the present invention, a minimally invasive surgical instrument comprises a shaft, an end effector connected to one end of the shaft, and a handle unit connected to the other end of the shaft. The handle unit includes a pair of linearly moving members, at least one rotating member for moving the pair of linear moving members away from each other in opposite directions, and a driving element for driving said at least one rotating member. The pair of
(Continued)

linearly moving members operates the end effector in the pitch direction or in the yaw direction.

12 Claims, 14 Drawing Sheets

(51) Int. Cl.
*A61B 17/29* (2006.01)
*A61B 17/00* (2006.01)

(52) U.S. Cl.
CPC ............... *A61B 2017/00398* (2013.01); *A61B 2017/2925* (2013.01); *A61B 2017/2927* (2013.01)

(58) Field of Classification Search
CPC ............ A61B 34/70; A61B 2017/2929; A61B 2017/00292; A61B 2017/003; A61B 2017/00318; A61B 2017/00323; A61B 2017/00327; A61B 2017/00353; A61B 19/22; A61B 2013/301
See application file for complete search history.

(56) References Cited

U.S. PATENT DOCUMENTS

| | | | |
|---|---|---|---|
| 2010/0076433 A1* | 3/2010 | Taylor | A61B 18/1445 606/52 |
| 2010/0087818 A1 | 4/2010 | Cunningham et al. | |
| 2010/0089974 A1* | 4/2010 | Shelton, IV | A61B 17/07207 227/180.1 |
| 2010/0179540 A1* | 7/2010 | Marczyk | A61B 18/1445 606/41 |
| 2012/0179151 A1* | 7/2012 | Mueller | A61B 17/29 606/33 |

* cited by examiner

_US 10,166,075 B2_

MINIMALLY INVASIVE SURGICAL INSTRUMENT IMPLEMENTING A MOTOR

FIELD OF THE INVENTION

The present invention relates to a minimally invasive surgical instrument implemented with a motor.

BACKGROUND

Minimally invasive surgery is a surgical approach that involves the use of instruments inserted through several tiny incision openings to perform a surgery causing minimal tissue trauma in human or animal bodies.

The minimally invasive surgery relatively reduces changes in metabolism of a patient in the period of post-surgical care, so it facilitates rapid recovery of the patient. Therefore, the minimally invasive surgery shortens the length of hospitalization of the patient after the surgery and allows the patient to return to normal physical activities in a short period of time. In addition, the minimally invasive surgery causes less pain and leaves fewer scars on the patient's body after the surgery.

One of the general forms of the minimally invasive surgery is endoscopy. Among the others, a laparoscopy that involves minimally invasive inspection and operation inside abdominal cavity is known as the most general form of endoscopy. To operate a standard laparoscopic surgery, the abdomen of the patient is insufflated with gas and at least one small incision is formed to provide an entrance for laparoscopic surgical instruments, through which a trocar is inserted. When performing the surgery, it is general that a user puts the laparoscopic surgical instruments into a surgical site or the like through the trocar, and manipulates (or controls) the instruments from the outside of abdominal cavity. In general, the laparoscopic surgical instruments include a laparoscope (for observation of a surgical site) and other working tools. Herein, the working tools are similar to the conventional tools used for small incision surgery, except that the end effector or working end of each tool is separated from its handle or the like by a shaft. For instance, the working tools may include a clamp, a grasper, scissors, a stapler, a needle holder, and so forth. Meanwhile, the user monitors the procedure of the surgery through a monitor that displays the images of the surgical site which are taken by the laparoscope. The endoscopic approaches similar to the above are broadly used in retroperitoneoscopy, pelviscopy, arthroscopy, cisternoscopy, sinuscopy, hysteroscopy, nephroscopy, cystoscopy, urethroscopy, pyeloscopy, and so on.

The inventor(s) has developed various minimally invasive surgical instruments useful for the above-mentioned minimally invasive surgeries and has already disclosed the features of the structures and effects of the same in Korean Patent Application Nos. 2008-51248, 2008-61894, 2008-79126 and 2008-90560, the contents of which are incorporated herein by reference in its entirety. Additionally, the inventor(s) have also introduced a minimally invasive surgical instrument with improved functionality, which is more advantageous for users and patients, in Korean Patent Application Nos. 2010-115152, 2011-3192, 2011-26243 and 2011-29771, the contents of which are incorporated herein by reference in its entirety.

Herein, the inventor(s) now present a minimally invasive surgical instrument that may employ a motor and that a user may hold and manipulate more conveniently than those disclosed in the above Korean applications or others.

SUMMARY OF THE INVENTION

One object of the present invention is to provide a minimally invasive surgical instrument that may employ a motor and that a user may hold and manipulate more conveniently.

Another object of this invention is to provide a minimally invasive surgical instrument that may be easily combined with a separate system (e.g., a surgical robot system).

Yet another object of this invention is to provide a minimally invasive surgical instrument wherein mechanical instability is minimized.

According to one aspect of the invention to achieve the objects as described above, there is provided a minimally invasive surgical instrument comprising a shaft; an end effector being connected to one end of the shaft; and a handling unit being connected to the other end of the shaft, wherein the handling unit comprises a pair of linear motion members; at least one rotating member to allow the pair of linear motion members to move in the opposite directions; and a driving element to drive the at least one rotating member, and wherein the pair of linear motion members operates the end effector in a pitch or yaw direction.

In addition, there may be provided other configurations to implement this invention.

According to the invention, there is provided a minimally invasive surgical instrument that may employ a motor and that a user may hold and manipulate more conveniently.

According to the invention, there is provided a minimally invasive surgical instrument that may be easily combined with a separate system (e.g., a surgical robot system).

According to the invention, there is provided a minimally invasive surgical instrument wherein mechanical instability is minimized.

DETAILED DESCRIPTION OF THE PREFERRED EMBODIMENTS

Figure 1:
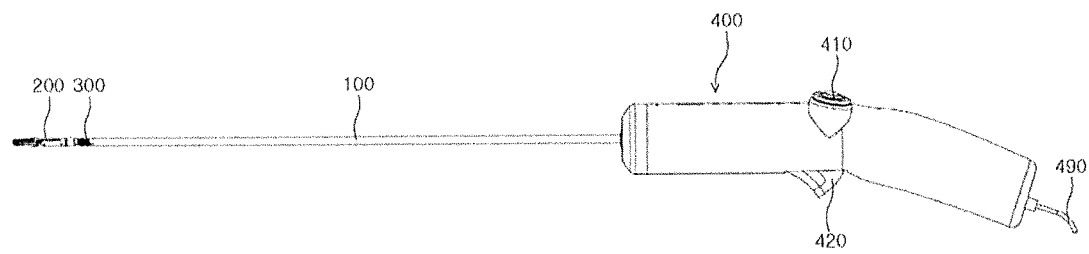
FIG. 1 shows the overall appearance of a minimally invasive surgical instrument according to one embodiment (a first embodiment) of the invention.

In the following detailed description of the invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, or characteristics described herein may be implemented as modified from one embodiment to another embodiment without departing from the spirit and the scope of the invention. Furthermore, it shall be understood that the locations or arrangements of individual elements within each embodiment may be also modified without departing from the spirit and the scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, preferred embodiments of the present invention will be described in detail with reference to the accompanying drawings to enable those skilled in the art to easily implement the invention.

Meanwhile, it should be understood that the term "connection" herein encompasses a direct connection or an indirect connection (i.e., via separate components) between mechanical or other types of components. For example, a connection between two rotating components may be a direct connection by the engagement of corresponding gear elements or the like, but may also be an indirect connection via a separate component such as a cable or another rotating component.

First Embodiment

FIG. 1 shows the overall appearance of a minimally invasive surgical instrument according to one embodiment (a first embodiment) of the invention.

Reference will be made to FIG. 1. The minimally invasive surgical instrument may comprise a shaft 100; an end effector 200 being connected to one end of the shaft 100 to perform surgery by using surgical tools (not shown) or functioning itself as a surgical tool; a joint unit 300 to connect the shaft 100 and the end effector 200 and to provide the end effector 200 with joint functionality; and a handling unit 400 being connected to the other end of the shaft 100 and capable of being held and manipulated by a user.

First, the shaft 100 may include a cavity therein to support and pass at least one wire or torque transmission member, in the same manner as those of the minimally invasive surgical instruments disclosed in the aforementioned Korean patent applications of the applicant(s). (The torque transmission member is mainly intended for the rolling motion of the end effector 200, while the shaft 100 may function itself as the torque transmission member in some cases.) The shaft 100 may comprise at least one segment as necessary. Further, the shaft 100 may comprise a bend in at least a part thereof.

Next, the end effector 200 may carry out joint motion, rolling motion, opening/closing motion and the like by the action of the at least one wire or torque transmission member passing from the handling unit 400 to the joint unit 300 via the shaft 100, in the same manner as those of the minimally invasive surgical instruments disclosed in the aforementioned Korean patent applications of the applicant(s). The tip of the end effector 200 may be implemented in the form of a clamp, a grasper, a pair of scissors, a stapler, a needle holder, a hook-type electrode or the like.

Next, the joint unit 300 may act together with the at least one wire or torque transmission member to allow the end effector 200 to carry out joint motion, rolling motion and the like, in the same manner as those of the minimally invasive surgical instruments disclosed in the aforementioned Korean patent applications of the applicant(s).

Finally, the handling unit 400 may control the joint motion, rolling motion, opening/closing motion and the like of the end effector 200 according to the user's manipulation, in the same manner as those of the minimally invasive surgical instruments disclosed in the aforementioned Korean patent applications of the applicant(s). To allow for such control, the at least one wire or torque transmission member may be connected to the handling unit 400. Further, the handling unit 400 may comprise a multifunction manipulation unit 410 and a trigger 420 to allow the user to carry out various manipulations as will be described below. In addition, a power cord 490 may be connected to the handling unit 400 to supply power for driving at least one driving element (e.g., an electric motor) that may be included in the handling unit 400.

Figure 2:
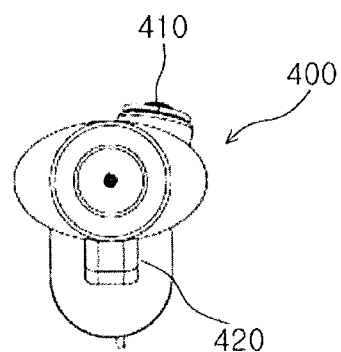
FIG. 2 is a front view of a handling unit 400 of the minimally invasive surgical instrument shown in FIG. 1.
Figure 3:
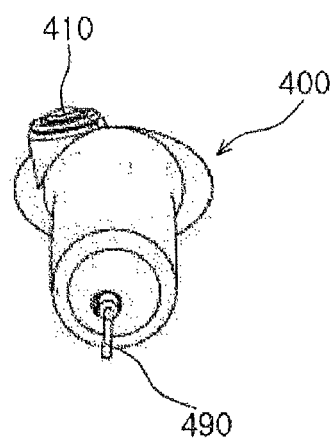
FIG. 3 is a rear view of the handling unit 400 of the minimally invasive surgical instrument shown in FIG. 1.

FIG. 2 is a front view of the handling unit 400 of the minimally invasive surgical instrument shown in FIG. 1, and FIG. 3 is a rear view of the handling unit 400 of the minimally invasive surgical instrument shown in FIG. 1.

Further reference will be made to FIGS. 2 and 3. In the handling unit 400, the multifunction manipulation unit 410 may be disposed at the position to enable the user to conveniently manipulate the handling unit 400 using only one finger (e.g., thumb) while holding it with the right hand. It is apparent that the multifunction manipulation unit 410 may also be disposed in the handling unit 400 to be suitable for the left-hand grip as necessary. Therefore, the user may use a set of minimally invasive surgical instruments for the right-hand and left-hand grip in some cases.

Figure 4:
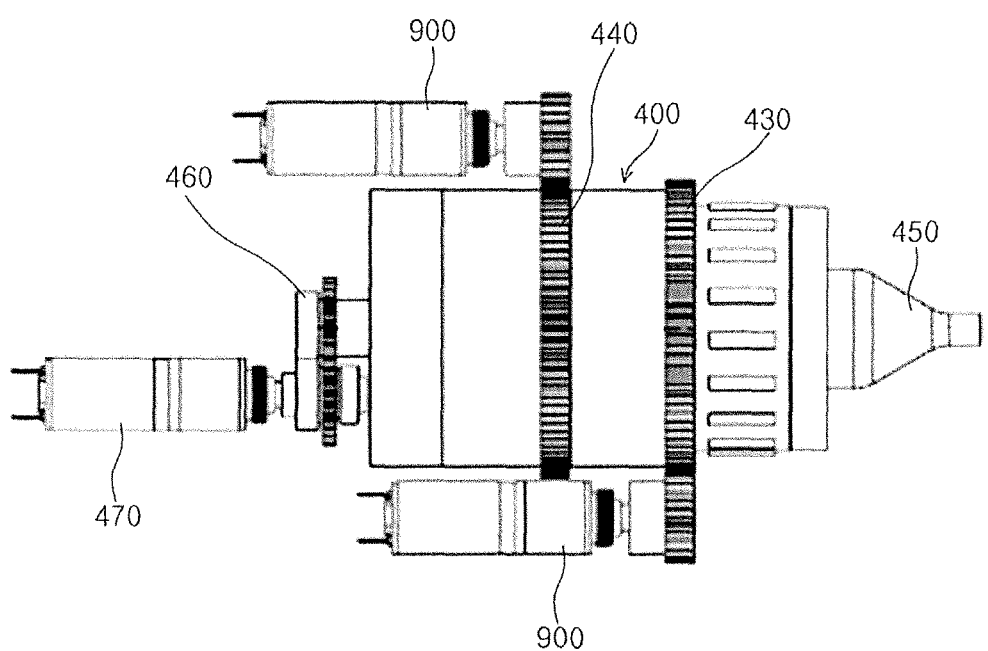
FIG. 4 shows some components of the handling unit 400 of the minimally invasive surgical instrument according to one embodiment of the invention.

FIG. 4 shows some components of the handling unit 400 of the minimally invasive surgical instrument according to one embodiment of the invention.

Reference will be made to FIG. 4. The handling unit 400 may comprise a first gear 430, a second gear 440, a guide 450, a first rotating member 460 and a first driving element 470. Further, an external driving element 900 may be connected to the outer circumference of the first or second gear 430 or 440 as necessary.

First, the first and second gears 430 and 440 may be disposed and rotate along the outer circumference of the handling unit 400 (at least a part of which is preferably cylindrical). The first or second gear 430 or 440 may have a gear element at the inner circumference thereof or at the inner and outer circumferences thereof. Meanwhile, the first and second gears 430 and 440 may be disposed substantially parallel to each other.

Next, the guide 450 may be configured in the form of a cone, hemisphere or pyramid, or in the form similar to one or more of the foregoing, so that a pitch wire (not shown) and a yaw wire (not shown) from linear motion members to be described below and an opening/closing wire or a torque transmission member to be described below may be guided to the cavity of the shaft 100. As descried above, the above wires or torque transmission member may act on the joint unit 300 or the end effector 200 to cause the joint motion, rolling motion, opening/closing motion and the like of the end effector 200.

Next, the first rotating member 460 may be driven by the first driving element 470 to be described below to allow the rotation of a torque transmission member that may be connected to one end thereof not shown in the drawing. To this end, the first rotating member 460 may have a gear element for connection to the first driving element 470 at one end thereof shown in the drawing.

Finally, at least a part of the first driving element 470 may be an electric motor. The electric motor may be driven by the power supplied through the power cord 490. The first driving element 470 may have a gear element for connection to the first rotating member 460 at one end thereof shown in the drawing.

Figure 5:
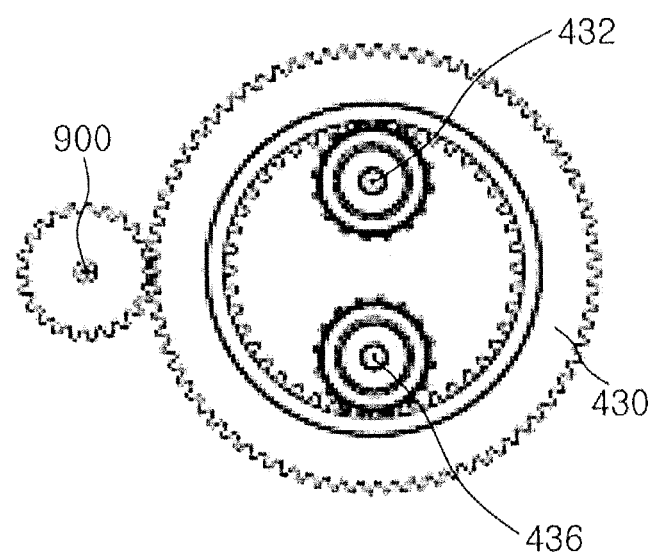
FIG. 5 is a cross-sectional view of some components of the handling unit 400 of the minimally invasive surgical instrument shown in FIG. 4.

FIG. 5 is a cross-sectional view of some components of the handling unit 400 of the minimally invasive surgical instrument shown in FIG. 4.

Further reference will be made to FIG. 5. A second rotating member 432 and a third rotating member 436, which are paired to each other, may be connected to the inner circumference of the first gear 430. To this end, the second and third rotating members 432 and 436 may have gear elements as shown in the drawing. Therefore, the second and third rotating members 432 and 436 may always rotate at substantially the same angular velocities with respect to each other as at least one (preferably, only one) of them is driven by a driving element such as an electric motor (not shown but may be referred to as a second driving element). Further, the second and third rotating members 432 and 436 may rotate together according to the rotation of the first gear 430 being connected with and driven by the external driving element 900. To this end, the external driving element 900 may have a gear element as shown in the drawing.

Meanwhile, although the first gear 430 and the associated components have been mainly described above, those skilled in the art will understand that the second gear 440 and the associated components (not shown but may be referred to as a fourth rotating member, a fifth rotating member, a third driving element and the like for convenience) may also have the same configurations. The first and second gears 430 and 440 (as well as the pair of the second and third rotating members 432 and 436 and the pair of the fourth and fifth rotating members) may rotate independently of each other to cause the independent operations of the pitch wire and yaw wire (or the yaw wire and pitch wire), respectively, according to the unique principle of the present invention to be described below.

Figure 6:
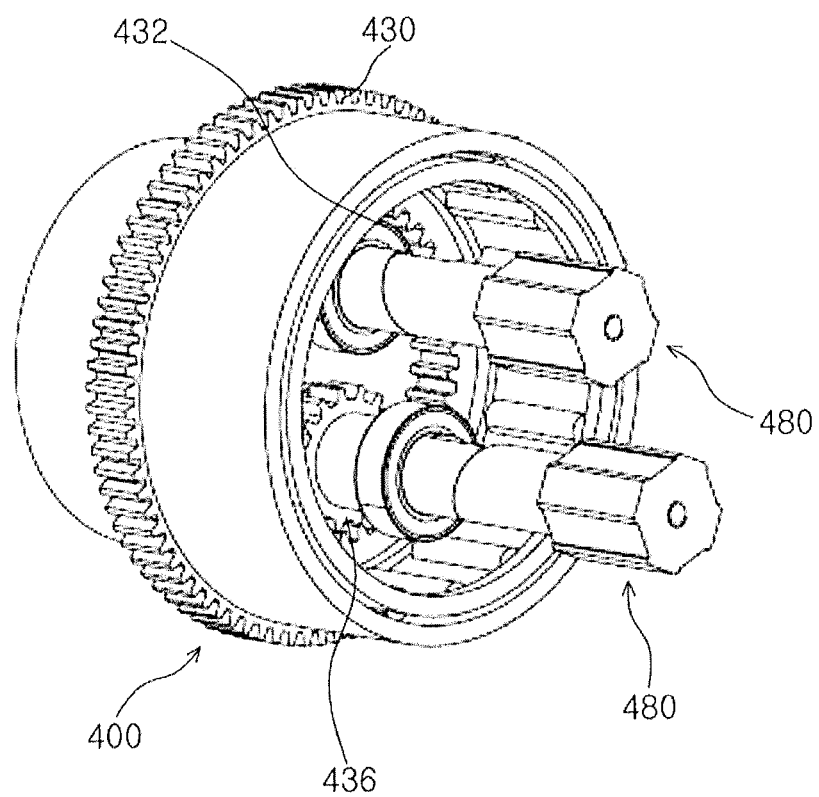
FIG. 6 is a perspective view of some components of the handling unit 400 of the minimally invasive surgical instrument shown in FIG. 4.
Figure 7:
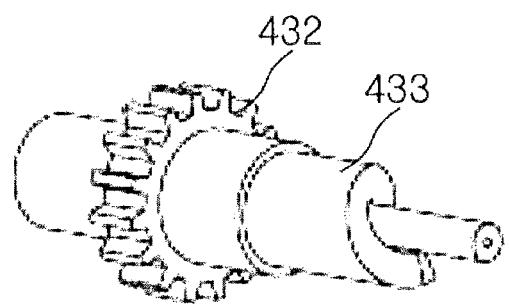
FIG. 7 is a perspective view of a second rotating member 432.
Figure 8:
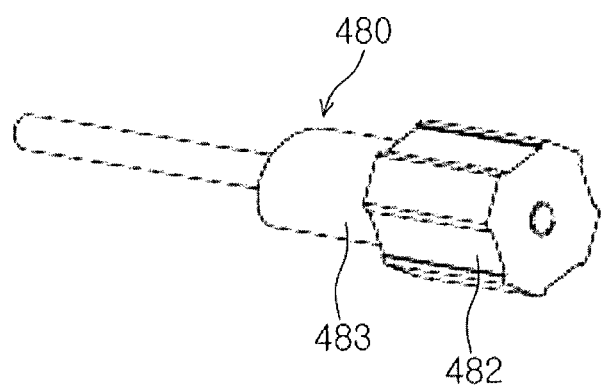
FIG. 8 is a perspective view of one linear motion member 480.

FIG. 6 is a perspective view of some components of the handling unit 400 of the minimally invasive surgical instrument shown in FIG. 4. FIG. 7 is a perspective view of the second rotating member 432, and FIG. 8 is a perspective view of one linear motion member 480.

Further reference will be made to FIGS. 6 to 8. Under the condition shown in FIG. 6, the second and third rotating members 432 and 436 may allow each of a pair of linear motion members 480 to carry out forward and backward motion via a spiral part to be described below. In this case, each of the pair of linear motion members 480 may carry out forward and backward motion in the opposite directions and at substantially the same distance with respect to each other while grasping the pitch wire (or yaw wire) (or passing the pitch wire (or yaw wire)). Therefore, the pair of linear motion members 480 may control the joint unit 300 to cause the pitch direction (or yaw direction) operation of the end effector 200. In connection with the principle thereof, further reference may be made to those disclosed in the aforementioned Korean patent applications, particularly Korean Patent Application No. 2010-115152.

As shown in FIG. 7, a spiral part 433 may be connected or coupled to the second rotating member 432. Further, as shown in FIG. 8, one linear motion member 480 corresponding to the second rotating member 432 may comprise a wire fixing part 482 and a spiral part 483. In this case, each of the spiral part 433 and the corresponding spiral part 483 may have a spiral structure to allow the spiral part 483 to approach or go away from the spiral part 433 according to the rotation of the spiral part 433. Further, a corresponding spiral part may also be connected or coupled to the third rotating member 436, and another corresponding linear motion member 480 may comprise a corresponding wire fixing part 482 and a corresponding spiral part 483. However, the spiral orientation of the spiral part 433 of the second rotating member 432 is opposite to that of the corresponding spiral part of the third rotating member 436, and this also applies to the pair of spiral parts 483 of the pair of linear motion members 480. Thus, when the distance between the second rotating member 432, which may be fixed in the handling unit 400, and the corresponding linear motion member 480 is decreased (i.e., when the corresponding linear motion member 480 carries out backward motion in the direction away from the end effector 200), the distance between the third rotating member 436 and the corresponding linear motion member 480 is increased (that is, the corresponding linear motion member 480 carries out forward motion in the direction toward the end effector 200), and vice versa. Therefore, the pitch wire (or yaw wire) that the pair of wire fixing parts 482 of the pair of linear motion members 480 are grasping or at least passing may cause the above-described joint motion.

Figure 9:
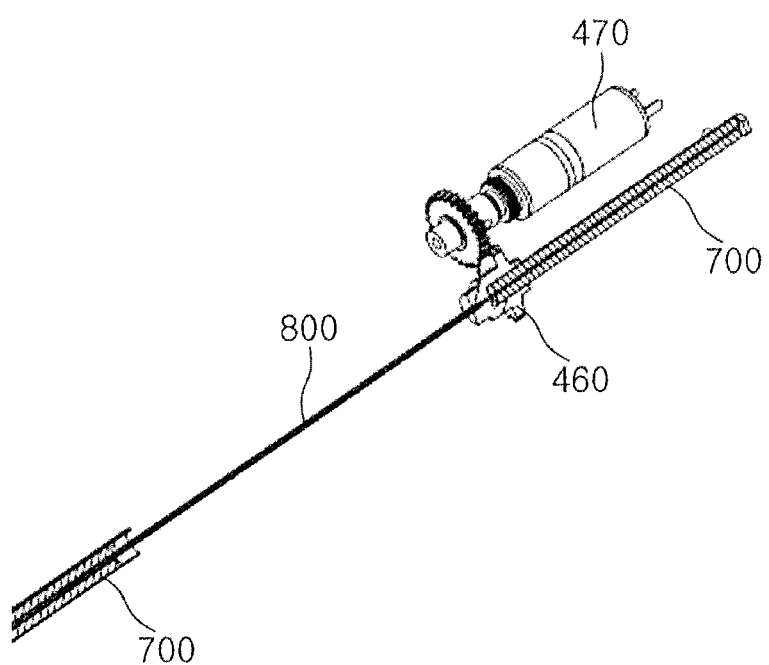
FIG. 9 is an exploded perspective view of some components of the handling unit 400 of the minimally invasive surgical instrument according to one embodiment of the invention.

FIG. 9 is an exploded perspective view of some components of the handling unit 400 of the minimally invasive surgical instrument according to one embodiment of the invention.

Reference will be made to FIG. 9. The first rotating member 460 may be driven by the first driving element 470 to rotate while holding a torque transmission member 700. In connection with the specific configuration of the torque transmission member 700, further reference may be made to those disclosed in the aforementioned Korean patent applications, particularly Korean Patent Application No. 2011-29771.

Meanwhile, an opening/closing wire 800 may preferably be passed through the interior of the torque transmission member 700. As the opening/closing wire 800 is pulled or released, the end effector 200 may carry out opening/closing motion as disclosed in the aforementioned Korean patent applications.

Figure 10:
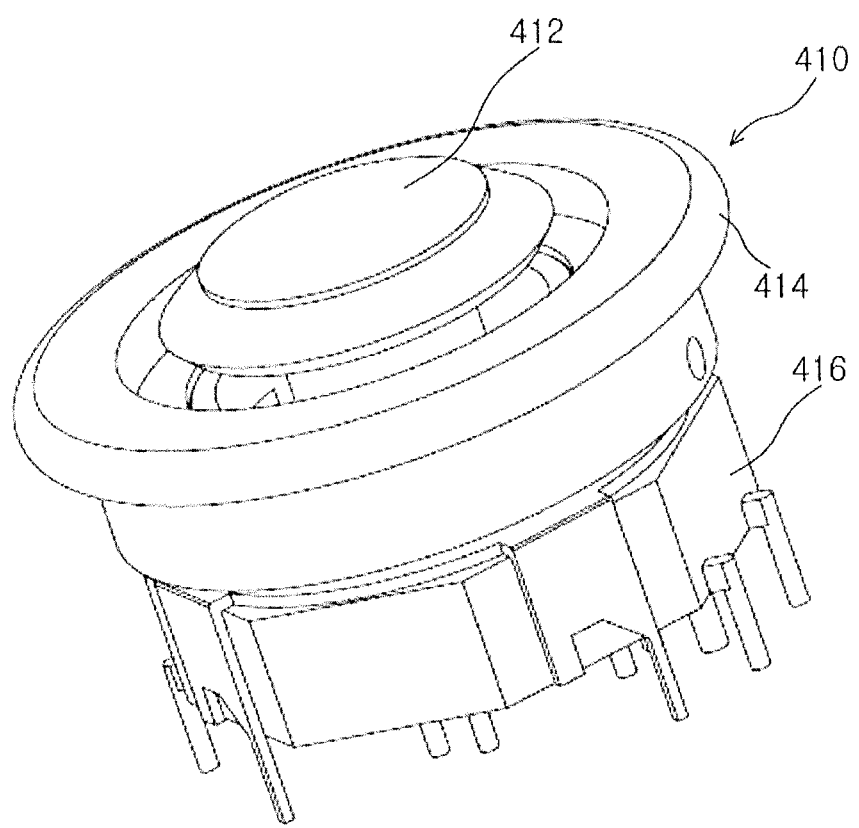
FIG. 10 shows in detail a multifunction manipulation unit 410 of the handling unit 400 of the minimally invasive surgical instrument according to one embodiment of the invention.

FIG. 10 shows in detail a multifunction manipulation unit 410 of the handling unit 400 of the minimally invasive surgical instrument according to one embodiment of the invention. As shown in FIG. 10, the multifunction manipulation unit 410 may comprise a joint manipulation unit 412, a rolling manipulation unit 414 and a fixing part 416.

First, the joint manipulation unit 412 may be manipulated in at least four directions (or in at least eight directions) in a manner similar to a joystick to control the pitch direction operation, yaw direction operation or bidirectional operation of the end effector 200. Further, the joint manipulation unit 412 may be pushed or released like a button to fix or release the joint motion state of the end effector 200. To this end, the handling unit 400 may further comprise an electronic circuit board (e.g., a printed circuit board) (not shown) for electronically detecting the direction in which the joint manipulation unit 412 is manipulated or whether it is pushed or not to drive or fix the above-described second or third driving element. It is apparent that the electronic circuit board may be readily implemented using known techniques.

Next, the rolling manipulation unit 414 may preferably be implemented in the form of a wheel to control the rolling motion of the end effector 200. To this end, the handling unit 400 may further comprise an electronic circuit board (e.g., a printed circuit board) (not shown) for electronically detecting the rotation of the rolling manipulation unit 414 to drive the above-described first driving element 470. It is apparent that the electronic circuit board may also be readily implemented using known techniques.

Finally, the fixing part 416 may provide electrical connections required for the above-described electronic configurations and mechanically fix the multifunction manipulation unit 410 to the handling unit 400.

Meanwhile, the trigger 420, which is shown in FIGS. 1 and 2 but not described in detail, will be discussed below. The trigger 420 may control the pulling or release of the opening/closing wire 800. For example, when the trigger 420 is pushed, the opening/closing wire 800 may be fixed in a pulled state (thus, for example, the end effector 200 may be closed and remain in that state). Otherwise, the pulling of the opening/closing wire 800 may be released (thus, for example, the end effector 200 may be opened).

Second Embodiment

According to the present embodiment, there is provided a minimally invasive surgical instrument comprising a handling unit 400' having a configuration slightly different from that of the handling unit 400 according to the first embodiment of the invention.

Figure 11:
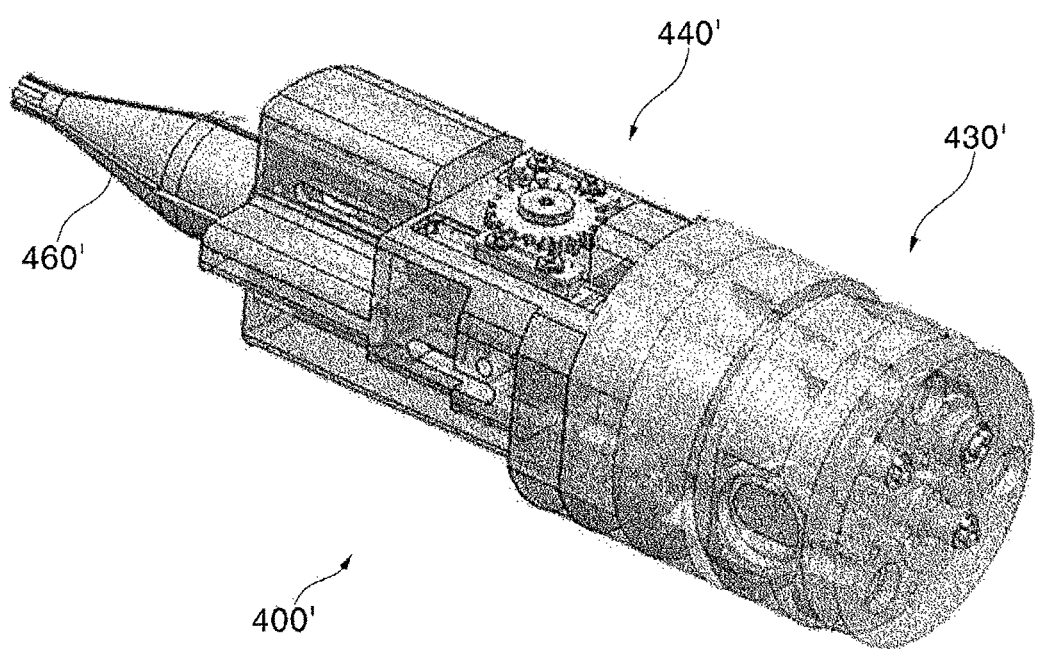
FIG. 11 shows a handling unit 400' of a minimally invasive surgical instrument according to another embodiment (a second embodiment) of the invention.

FIG. 11 shows the handling unit 400' of the minimally invasive surgical instrument according to another embodiment (a second embodiment) of the invention.

Reference will be made to FIG. 11. The handling unit 400' may be roughly divided into a first section 430' and a second section 440'. The first and second sections 430' and 440' may preferably be configured to separate from each other. According to this configuration, if the first section 430' is damaged, for example, then only the first section 430' may be replaced by a new one. The components included in the first and second sections 430' and 440' of the handling unit 400' will be described later.

Further, the handling unit 400' may comprise a guide 460'. The guide 460' may be configured in the form of a cone, hemisphere or pyramid, or in the form similar to one or more of the foregoing, so that a pitch wire (not shown) and/or a yaw wire (not shown) from a sliding block to be described below and/or an opening/closing wire (not shown) and/or torque transmission member to be described below may be guided to the cavity of the shaft 100. As described above, the above wires or torque transmission member may act on the joint unit 300 or the end effector 200 to cause the joint motion, rolling motion, opening/closing motion and the like of the end effector 200.

Figure 12:
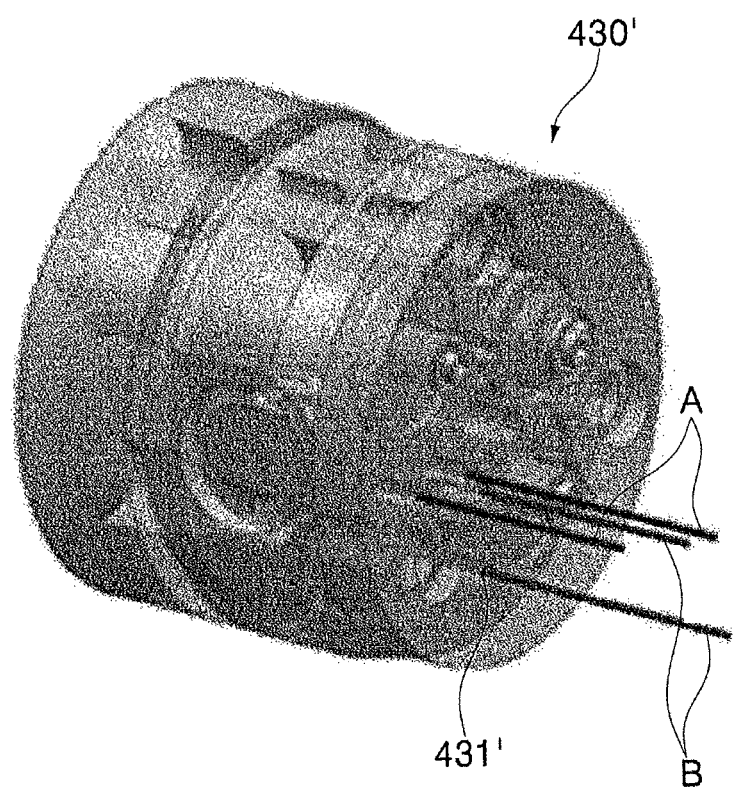
FIG. 12 shows a first section 430' of the handling unit 400'.
Figure 13:
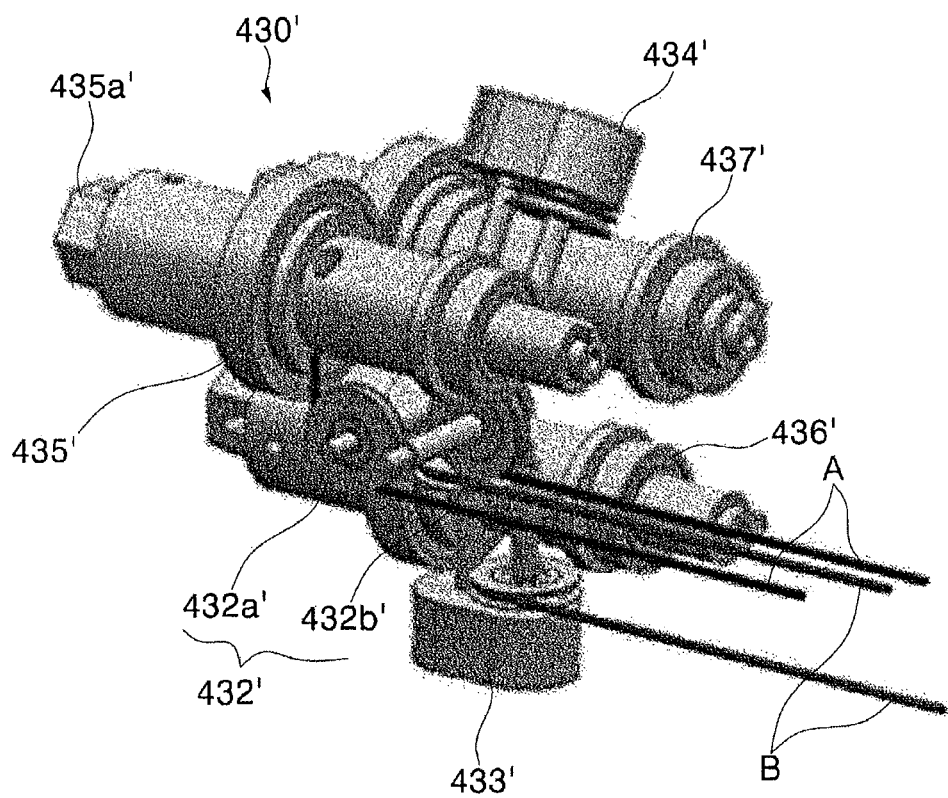
FIG. 13 shows the (internal) components of the first section 430' shown in FIG. 12.

FIG. 12 shows the first section 430' of the handling unit 400', and FIG. 13 shows the (internal) components of the first section 430' shown in FIG. 12.

Reference will be made to FIGS. 12 and 13. There may be formed in the first section 430' (preferably a plurality of) wire through-holes 431'. In addition, a wire A and/or wire B may be further arranged. The wire A and/or wire B may be disposed through the wire through-holes 431'. On the one hand, the wires A, B may be connected to at least one (preferably two different) electric motors (not shown), respectively. On the other hand, they may be connected to a first rotating member 435' or a second rotating member 436', respectively, to rotate the first or second rotating member 435' or 436' by means of the power of the electric motors, thereby causing the pitch direction or yaw direction operation of the end effector 200. Meanwhile, a rolling wire (not shown) may be further disposed through the through-holes 431' if necessary. The rolling wire may be connected to (another) electric motor on the one hand and connected to a third rotating member 437' on the other hand to rotate the third rotating member 437' by means of the power of the electric motor, thereby causing the roll direction operation of the end effector 200.

As shown, the wire A may be connected to the first rotating member 435' via a first set of pulleys 432' (e.g., a pair of pulleys 432a' and 432b'). When the wire A transmits rotation from the electric motor to the first rotating member 435', the first set of pulleys 432' may serve to change the rotation axis thereof. Further, the first rotating member 435' may comprise an insert 435a'. The insert 435a' may be inserted and fixed to a first linear motion converting member to facilitate the rotation of the first linear motion converting member according to the rotation of the first rotating member 435'. Meanwhile, the wire A may be led into and wound within the first rotating member 435' as shown, but may also be otherwise configured.

In the same manner, the wire B and the rolling wire may be connected to the second or third rotating member 436' or 437' via a second or third set of pulleys 433' or 434', respectively. In the above case, the second or third rotating member 436' or 437' may be configured similarly to the first rotating member 435', and the second or third set of pulleys 433' or 434' may also be configured similarly to the first set of pulleys 432'.

Figure 14:
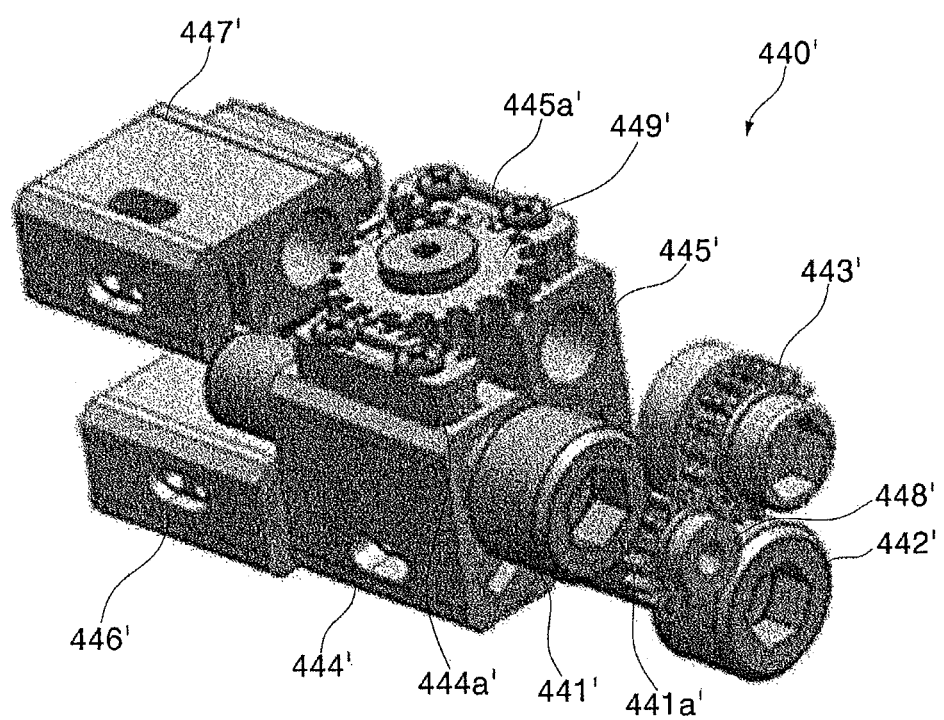
FIG. 14 shows the (internal) components of a second section 440' of the handling unit 400'.
Figure 15:
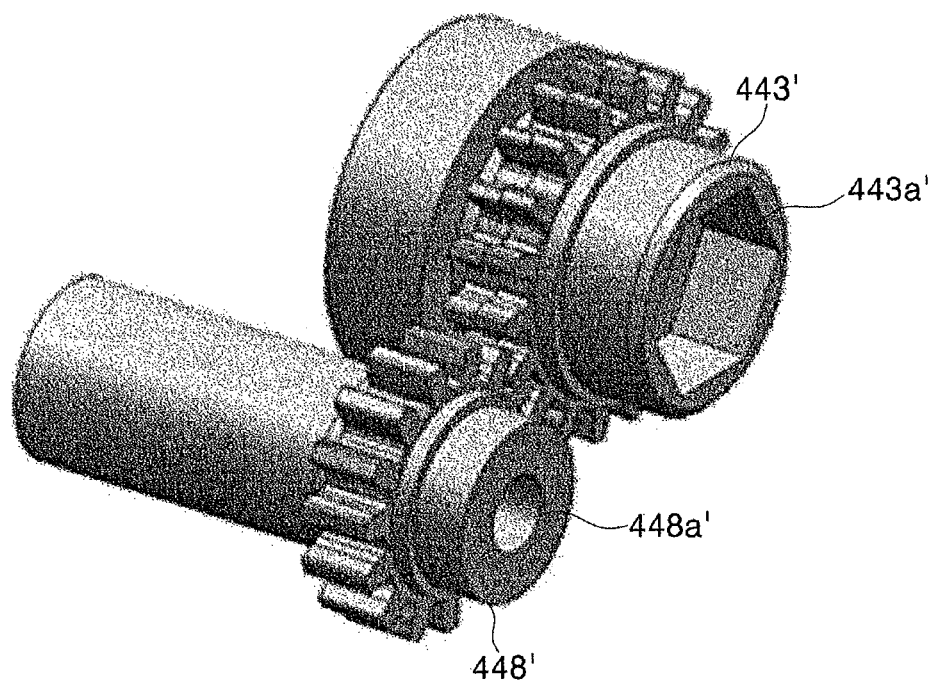
FIG. 15 shows some components thereof.

FIG. 14 shows the (internal) components of the second section 440' of the handling unit 400', and FIG. 15 shows some components thereof.

Further reference will be made to FIGS. 14 and 15. The second section 440' may include a first linear motion converting member 441' therein. The first linear motion converting member 441' may include a recess 441a' in which the insert 435a' of the first rotating member 435' may be inserted to receive rotation from the first rotating member 435'. Further, the first linear motion converting member 441' may include a screw thread (not shown) on a part of the surface thereof. The first linear motion converting member 441' may be fixed to some part in the second section 440' so that it may not carry out forward and backward motion other than rotational motion around the longitudinal axis thereof as the rotation axis. Meanwhile, the second section 440' may further comprise a first sliding block 444' that may carry out linear motion. The first sliding block 444' may include a screw groove (not shown) in a through-hole (not shown) therein. Thus, when the first linear motion converting member 441' fixed to some part in the second section 440' rotates according to the rotation of the first rotating member 435', the first sliding block 444' with the first liner motion converting member 441' being inserted in the corresponding through-hole may carry out linear motion in forward or backward direction.

As the first sliding block 444' carries out the linear motion, a first rack element 444a' that may be formed on the first sliding block 444' may also carry out linear motion together. This may cause the rotation of a pinion gear 449' that may be arranged engaging with the first rack element 444a' as shown. Then, this may lead to the linear motion of a second rack element 445a' that may be disposed opposite to the first rack element 444a' across the pinion gear 449'. Therefore, the first and second rack elements 444a' and 445a' may carry out linear motion in the opposite directions and at substantially the same distance with respect to each other. Accordingly, a second sliding block 445', which may also be included in the second section 440' and comprise the second rack element 445a', may also carry out linear motion in the opposite direction and at substantially the same distance with respect to the linear motion of the first sliding block 444'.

Meanwhile, the second section 440' may further include therein a second linear motion converting member 442', a third sliding block 446' and a fourth sliding block 447'. The configurations and operating principles of these components may be similar to those of the above-described components.

Further, the second section 440' may further include therein a first gear 443' and a second gear 448'. The first gear 443' may include a recess 443a' in which an insert (not shown) of the third rotating member 43T may be inserted to receive rotation from the third rotating member 437'. The first gear 443' may engage with the second gear 448'. The second gear 448' may be connected to or integrated with the torque transmission member. Therefore, when the first gear 443' rotates according to the rotation of the third rotating member 437', the second gear 448' rotates to eventually cause the rolling motion of the end effector 200'. Meanwhile, an opening/closing wire through-hole 448a' may be formed in the second gear 448'. Thus, the opening/closing wire may be disposed in the handling unit 400'.

Figure 16:
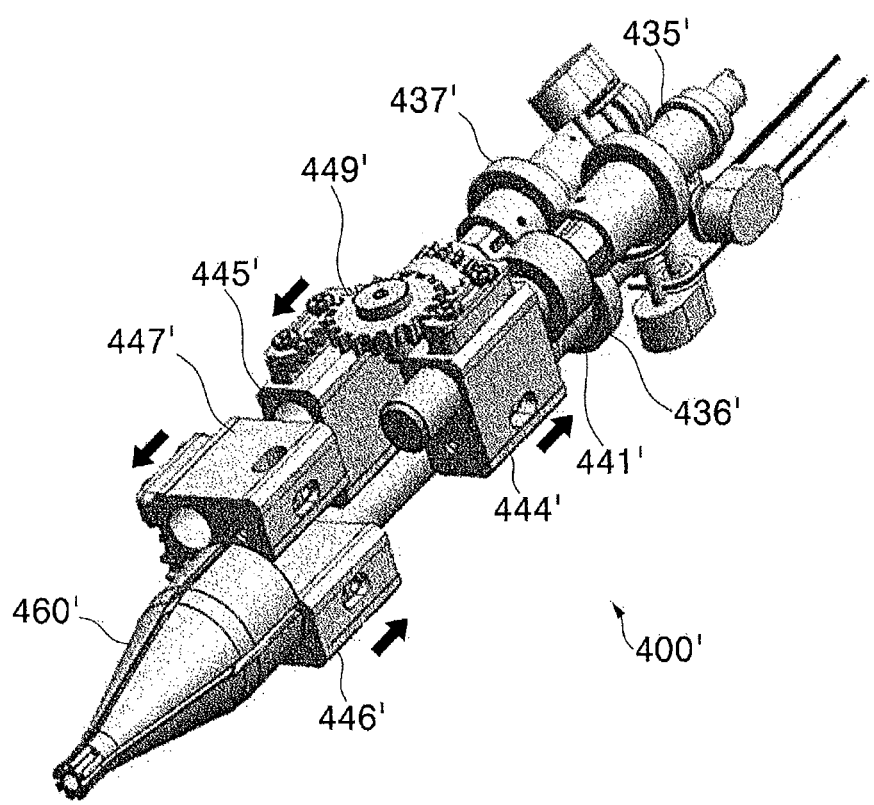
FIG. 16 shows the operation of the handling unit 400' of the minimally invasive surgical instrument according to another embodiment of the invention.

FIG. 16 shows the operation of the handling unit 400' of the minimally invasive surgical instrument according to another embodiment of the invention.

Further reference will be made to FIG. 16. As described above, when the wire A transmits rotation from the electric motor to the first rotating member 435', this may eventually cause the first and second sliding blocks 444' and 445' to carry out linear motion in the opposite directions. In this case, each of the first and second sliding blocks 444' and 445' may carry out forward and backward motion in the opposite directions and at substantially the same distance with respect to each other while grasping the pitch wire (or yaw wire). The pitch wire (or yaw wire) may be guided to the cavity of the shaft 100 along the guide 460' and connected to the joint unit 300. Therefore, the first and second sliding blocks 444' and 445' may control the joint unit 300 to cause the pitch direction (or yaw direction) operation of the end effector 200. In the same manner, each of the third and fourth sliding blocks 446' and 447' may carry out forward and backward motion in the opposite directions and at substantially the same distance with respect to each other while grasping the yaw wire (or pitch wire). Therefore, the third and fourth sliding blocks 446' and 447' may cause the yaw direction (or pitch direction) operation of the end effector 200. In connection with the principle thereof, further reference may be made to those disclosed in the aforementioned Korean patent applications, particularly Korean Patent Application No. 2010-115152.

Applications

According to an application of the present invention, the minimally invasive surgical instrument may be connected with a driving element (e.g., the external driving element 900) of another motor-based system (not shown) such as a surgical robot as necessary, so that the end effector 200 may carry out joint motion without requiring the action of the internal driving elements. To this end, the form and the like of the handling unit 400, 400' may be partially modified to be suitable for the connection to another motor-based system. Further, the form and the like of the handling unit 400, 400' may be partially modified to enable the end effector 200 to carry out rolling motion or opening/closing motion by means of another motor-based system as necessary.

Although the present invention has been described in terms of specific items such as detailed elements as well as the limited embodiments and the drawings, they are only provided to help general understanding of the invention, and the present invention is not limited to the above embodiments. It will be appreciated by a person of ordinary skill in the art that various modifications and changes may be made from the above description.

Therefore, the spirit of the present invention shall not be limited to the above-described embodiments, and the entire scope of the appended claims and their equivalents will fall within the scope and spirit of the invention.

What is claimed is:
1. A minimally invasive surgical instrument comprising:
a shaft;
an end effector being connected to one end of the shaft; and
a handling unit being connected to the other end of the shaft,
wherein the handling unit comprises:
 a pair of linear motion members to operate the end effector in one of a pitch direction and a yaw direction;
 another pair of linear motion members to operate the end effector in the other of the pitch direction and the yaw direction;
 a pair of rotating members to allow the pair of linear motion members to move in opposite directions;
 a first spiral part being coupled to one of the pair of rotating members and configured to move one of the pair of linear motion members;
 a second spiral part being coupled to the other of the pair of rotating members, configured to move the other of the pair of linear motion members, and having a spiral orientation opposite to that of the first spiral part;
 another pair of rotating members to allow the another pair of linear motion members to move in opposite directions;
 a driving element to drive the pair of rotating members; and
 another driving element to drive the another pair of rotating members,
wherein one of the pair of rotating members and the corresponding one of the pair of linear motion members are connected to each other via the first spiral part, and the other of the pair of rotating members and the other corresponding one of the pair of linear motion members are connected to each other via the second spiral part, wherein each of the pair of rotating members is connected with a common outer circumference rotating member disposed along an outer circumference of the handling unit, wherein each of the another pair of rotating members is connected with another common outer circumference rotating member disposed along the outer circumference of the handling unit, and wherein the common outer circumference rotating member and the another common outer circumference rotating member are capable of rotating independently of each other.

2. A minimally invasive surgical instrument as claimed in claim 1, wherein the common outer circumference rotating member is capable of being connected with an external driving element.

3. A minimally invasive surgical instrument as claimed in claim 1, wherein the handling unit further comprises another rotating member and another driving element to drive the another rotating member, and wherein the another rotating member allows the end effector to carry out rolling motion.

4. A minimally invasive surgical instrument as claimed in claim 3, wherein the handling unit further comprises a rolling manipulation unit to allow the end effector to carry out rolling motion.

5. A minimally invasive surgical instrument as claimed in claim 1, further comprising an opening/closing wire.

6. A minimally invasive surgical instrument as claimed in claim 5, wherein the handling unit further comprises a trigger to allow the opening/closing wire to open or close the end effector.

7. A minimally invasive surgical instrument as claimed in claim 1, wherein the handling unit further comprises a joint manipulation unit to operate the end effector in the pitch or the yaw direction.

8. A minimally invasive surgical instrument as claimed in claim 7, wherein the joint manipulation unit is capable of fixing a joint motion state of the end effector.

9. A minimally invasive surgical instrument as claimed in claim 1, wherein the pair of linear motion members are connected to each other via a gear.

10. A minimally invasive surgical instrument as claimed in claim 1, wherein at least one of the pair of rotating members and at least one of the pair of linear motion members are connected to each other via at least one linear motion converting member comprising a screw structure, and wherein the linear motion converting member rotates together according to rotation of the corresponding rotating member.

11. A minimally invasive surgical instrument as claimed in claim 1, wherein one of the pair of rotating members is configured to move one of the pair of linear motion members in one direction, and the other of the pair of rotating members is configured to move the other of the pair of linear motion members in another direction opposite to the one direction.

12. A minimally invasive surgical instrument as claimed in claim 1, wherein one of the another pair of rotating members is configured to move one of the another pair of linear motion members in one direction, and the other of the another pair of rotating members is configured to move the other of the another pair of linear motion members in another direction opposite to the one direction.

* * * * *